United States Patent [19]

Hudson

[11] Patent Number: 5,233,044

[45] Date of Patent: Aug. 3, 1993

[54] ACTIVE ESTERS FOR SOLID PHASE PEPTIDE SYNTHESIS

[75] Inventor: Derek Hudson, Anselmo, Calif.

[73] Assignee: Millipore Corporation, Bedord, Mass.

[21] Appl. No.: 766,895

[22] Filed: Sep. 26, 1991

Related U.S. Application Data

[63] Continuation of Ser. No. 362,980, Jun. 8, 1989, abandoned.

[51] Int. Cl.$^5$ ............................................ C07D 231/00
[52] U.S. Cl. ................................. 548/110; 548/363.1; 548/371.1; 548/375; 548/376; 548/368.1
[58] Field of Search ............... 548/363, 367, 375, 376, 548/363.1, 371.1, 110

[56] References Cited

U.S. PATENT DOCUMENTS 4,800,166  5/1989  Horn et al. .

FOREIGN PATENT DOCUMENTS 0208874  1/1987  European Pat. Off. .
86305480.5  1/1987  European Pat. Off. .
88710054.3  6/1989  European Pat. Off. .
WO87/04713  8/1987  PCT Int'l Appl. .

OTHER PUBLICATIONS

G. Losse et al. Leibigs Ann. Chem. 684 236–242 (1968).
Castro et al. Peptides: Proceedings of the European Peptide Symposium 79–84 (1976).
Dourtoglou et al. Communications (1984) at 572–574.
H. G. Garg and K. K. Shaunak (Aug. 18, 1975), *Chem. Abstr.* 83:(7):549, Abstract No.: 59255d.
H. G. Garg and K. K. Shaunak (1975) *Indian J. Chem.* 13(3):301–303.
G. Losse et al., *Leibigs Ann. Chem.,* 684:236–242 (1968) [Translated from German].
D. Hudson, *J. Organic Chemistry,* 53:617–624 (1988).
V. Dourtoglou and B. Gross, *Communications,* pp. 572–574 (1984).
R. Knorr et al., *Tetrahedron Letters,* 30:1927–1930 (1989).
B. Castro et al., In: *Peptides: Proceedings of the European Peptide Symposium,* pp. 79–84, A. Loffet (ed.), Editions Univ. Bruxelles, Brussels, Belgium (1976).

*Primary Examiner*—Merrell C. Cashion, Jr.
*Assistant Examiner*—Bennett Celsa
*Attorney, Agent, or Firm*—Hamilton, Brook, Smith & Reynolds

[57] ABSTRACT

Derivatives of 1-phenyl pyrazolin-5-one have many applications for biomolecule synthesis. Enol esters of protected amino acids made by the present process provide efficient coupling in solid-phase peptide synthesis. The 1-phenyl-pyrazolin-5-one derivatives are highly crystalline, stable, non-toxic and easy to prepare. Many possess self-indicating properties, facilitating spectrophotometric monitoring and automation of peptide synthesis.

7 Claims, No Drawings

ACTIVE ESTERS FOR SOLID PHASE PEPTIDE SYNTHESIS

This is a continuation of co-pending application Ser. No. 07/362,980 filed on Jun. 8, 1989, now abandoned.

BACKGROUND

The solid phase synthesis of peptides is a complex process which involves stepwise additions of aminoterminus-blocked amino acids to a peptide chain, the carboxyl terminus of which is attached to a solid support. Solid phase peptide synthesis (SPPS) typically begins with covalent attachment of the carboxyl end of a first alpha-amine protected amino acid through an organic linker to an insoluble resin synthesis bead. The general synthesis cycle then consists of deprotection of the alpha-amine group of the last amino acid, washing and, if necessary, neutralization, followed by reaction with a carboxyl-activated form of the next alpha-amine protected amino acid to be added. Each successive amino acid is attached to the terminal nitrogen by the carbonyl carbon of the carboxylic acid group.

Most present peptide synthesizers perform coupling with carbodi-imide reagents (e.g., with dicyclohexyl carbodi-imide (DCCI), or with diisopropylcarbodiimide (DIPCDI)). The synthesis is carried out in a reaction vessel which includes a synthesis resin therein.

After the coupling reaction is complete, the protected amino acid which is coupled through its carboxylic acid group to the synthesis resin is deblocked with a deblocking agent, such as trifluoroacetic acid (TFA) or piperidine, washed (when TFA is used) with a base and the next activated amino acid residue is added to the reaction vessel. Upon obtaining the desired peptide sequence, the peptide is cleaved from the synthesis support, generally either with anhydrous hydrogen fluoride (HF) or with TFA.

There are basically two ways of performing coupling in automated SPPS: with activated amino acid derivatives or with free amino acid derivatives which are activated prior to coupling. One advantage to using activated derivatives, such as active esters, is that these, if they are crystalline, can be highly pure and give clean couplings. A disadvantage to active esters is that if they are highly reactive, then they will be unstable in solution, and in long term storage in the solid state. Therefore, they must be stored as powders and dissolved prior to coupling.

Pentafluorophenyl (PFP) active esters are currently used in solid phase peptide synthesis and in solution synthesis. These derivatives suffer from the following disadvantages: they are made from pentafluorophenol, a highly toxic, costly and hygroscopic substance. Treatment of wastes is a problem. It is believed that PFP may contain dangerous, dioxin-like materials or give rise to such materials on storage; the pentafluorophenol liberated in this reaction is highly acidic, and protonates amino groups on the resin slowing the final stages of coupling. Since this would be an equilibrium process, protonation by this mild acid could not prevent the coupling from going to completion, but might slow the process; two PFP esters, serine (Ser) and threonine (Thr), are noncrystalline and so for these, alternative crystalline esters are used; and it is believed that the solution stability of PFP esters is insufficient. Thus, viable alternatives for the use of PFP-active esters are needed.

Available systems for solid phase peptide synthesis are described, for example, in U.S. Pat. Nos. 4,362,699, 4,531,258, 3,647,390 and 3,557,077. Ideally, the system should include a method for monitoring the completeness of each amino acid addition before the next amino acid is added to the peptide chain. Such a system would ensure the best possible yields of peptides. Some available methods for monitoring the amino acid synthesis reaction are described by G. Barany and B. Merrifield in "Selected Methods for Monitoring a Solid-Phase Peptide Synthesis", in *The Peptides*, Vol. 2, pp. 150–154 (1979).

Of the various methods for monitoring solid phase peptide synthesis, the most efficient and sensitive methods available to date to determine the presence of unreacted, or free, amino acids by detecting the amino groups. These methods genera.

Of the various methods for monitoring solid phase peptide synthesis, the most efficient and sensitive methods available to date to determine the presence of unreacted, or free, amino acids by detecting the amino groups. These methods generally involve stopping the reaction, and titrating the resin-bound amino groups with reagents which are reactive with the amino groups, and show a detectable response (e.g., colorimetric or potentiometric). These titration methods generally utilize acids, such as perchloric acid or picric acid, or halogen compounds which form halide salts, such as pyridine hydrochloride. These methods have several drawbacks, including the necessity of stopping the coupling reaction, destruction of some of the amino groups and reactivity with the peptide chain itself.

SUMMARY OF THE INVENTION

The present invention relates to compounds based on enol ester derivatives of 1-phenylpyrazolin-5-one which are useful in solid phase peptide synthesis, their use as activating groups for amino acids in solid phase peptide synthesis, their use as coupling reagents in solid phase peptide synthesis, and their utility in monitoring the coupling reaction. The invention further relates to activated amino acid esters containing the present compounds, and methods of making and using the compounds and activated amino acids in solid phase peptide synthesis.

The present compounds are enol esters of 1-phenylpyrazolin-5-one having the following general formula:

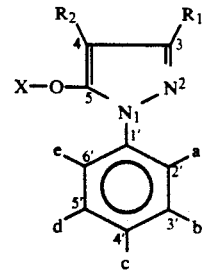

wherein $R_1$ is selected from the group consisting of: H, methyl ($CH_3$), ethyl ($CH_2CH_3$), isopropyl ($CH(CH_3)_2$), phenyl, nitrophenyl, chlorophenyl and benzyl, or simple variants thereof. A simple variant would include, for example, one or more substituents on the aromatic ring. $R_2$ is selected from the group consisting of: H, methyl ($CH_3$), ethyl ($CH_2CH_3$), isopropyl ($CH(CH_3)_2$), phenyl, nitrophenyl, chlorophenyl, benzyl, halogens (e.g., Cl, Br), nitro (NO$_2$) and azo derivatives (e.g., Ph—N=N—) or simple variants thereof. Additionally, R$_1$ and R$_2$ may represent a bridge between the 3 and 4 ring positions of the pyrazolinone ring, which bridge has from about 3 to about 8 methylene groups. The substituents a, b, c, d and e are selected from the group consisting of: H, NO$_2$, halogens and SO$_3$H; and X is selected from the group consisting of: formyl, acetyl, benzoyl, phenoxyacetyl and toluene sulfonyl 2,4,6-trimethyl benzene sulfonyl. X can also be a phosphonium salt, such as tris (dimethylamino) phosphonium hexafluorophosphate or tetrafluoroborate, a uronium salt such as tetramethyluronium hexafluorophosphate or tetrafluoroborate and derivatives of these compounds. Additionally, X represents amino acids and amine-protected amino acid derivatives, thereby forming activated amino acid derivatives. However, R$_1$ cannot be methyl if R$_2$, a, b, c, d and e are all represented by H, as the compound having this configuration, Mpp, has low activity, is generally formed in low yields, and is not self-indicating.

The present 1-phenyl-pyrazolin-5-one compounds are esterified through the carboxyl group of an amino acid to form an activated amino acid derivative. The amino acids are generally amine-protected amino acid derivatives having the general formula:

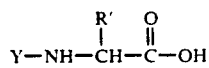

wherein R' represents the amino acid side chain and Y is a protective group, such as α-fluorenylmethyloxycarbonyl(Fmoc), t-butyloxy-carbonyl (tBoc), 2-(4-biphenylyl)-2-propyloxycarbonyl (Bpoc) and 2-nitropyridylsulfenyl (Npys).

The present compounds possess excellent properties for solid phase peptide synthesis. When added to a SPPS system, the compounds act as colorimetric indicators. Activated amino acid esters made from the present compounds are pure, crystalline, stable and are self-indicating. For example, amino acid esters of 3-methyl-1-(4'nitrophenyl)-2-pyrazolin-5-one (Npp), are highly crystalline, stable in solutions of solvents commonly used for SPPS (e.g., DMF) and are unreactive to hydroxyl groups. During coupling liberated Npp is ionized by unreacted amino groups giving an intense blood-red coloration to the support, which fades to the gold color of unionized Npp when the coupling is complete. This color change can be utilized to monitor the reaction for completion.

The present 1-phenyl-pyrazolin-5-one derivatives can be used as additives to known coupling reagents, can constitute new coupling reagents or be used as active esters of amino acids. As new coupling reagents, in solid phase peptide synthesis for example, where X is a phosphonium salt such as tris(dimethylamino)phosphonium hexafluorophosphate, the composition is added, along with one equivalent of a tertiary base to non-preactivated, α-amino-protected amino acid derivatives (also called "free" protected amino acids). The resultant activated species is then added to the support-bound peptide to effect coupling and chain elongation, and simultaneously liberating the 1-phenyl-pyrazolin-5-one moiety, which acts as the colorimetric indicator. Phosphonium derivatives of the present 1-phenyl-pyrozolin-5-one compounds can also be used as an alternative method to the DCCI procedure described herein for phenyl-pyrazolinone enol ester preparation.

The present 1-phenyl-pyrazolin-5-one derivatives are used to form activated amino acid esters having several desirable properties, including: they can be made from inexpensive, non-toxic materials; the byproduct liberated during coupling has low acidity, and spectral characteristics which allow its discrimination from the unreacted active ester, thereby allowing quantitation of coupling; they are highly crystalline; soluble in DMF, and can be prepared in high yield and purity by variety of methods, including the dicyclohexylcarbodiimide (DCCI) condensation method.

The properties of activated amino acid derivatives formed from the present compounds include high crystallinity and reactivity, stability, and selectivity to aminolysis rather than hydrolysis. Since amino acid esters of these compounds are relatively inert to the presence of hydroxyl groups, they may advantageously be used in the presence of hydrogen-bond-disrupting alcohols, such as 2,2,2-trifluoroethanol, thereby allowing difficult reactions which are hindered by peptide secondary structures and aggregation to go to completion. The use of these alcohols is unsuitable in SPPS where PFP, or other esters which are not inert to attack by hydroxyls, are used. The present activated amino acid esters are self-indicating, which facilitates the spectrophotometric monitoring and automation of solid phase peptide synthesis.

DETAILED DESCRIPTION OF THE INVENTION

The present compounds are enol derivatives of 1-phenyl-pyrazolin-5-one, having the following general formula:

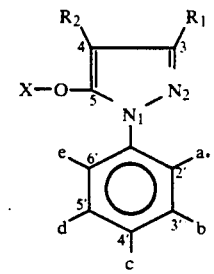

Wherein R$_1$ is selected from the group consisting of: H, methyl (CH$_3$), ethyl (CH$_2$CH$_3$), isopropyl (CH(CH$_3$)$_2$), phenyl, nitrophenyl, chlorophenyl and benzyl, or simple variant thereof. A simple variant would include, for example, are or more substituents on the aromatic ring. R$_2$ is selected from the group consisting of: H, methyl (CH$_3$), ethyl (CH$_2$CH$_3$), isopropyl (CH(CH$_3$)$_2$), phenyl, nitrophenyl, chlorophenyl, benzyl, halogens (e.g., Cl, Br), nitro (NO$_2$) and azo derivatives (e.g., Ph—N=N—) or simple variants thereof. Additionally, R$_1$ and R$_2$ may represent a bridge between the 3 and 4 ring positions, which bridge has from about 3 to about 8 methylene groups. The substituents a, b, c, d and e are selected from the group consisting of: H, NO$_2$, halogens and SO$_3$H; and X is selected from the group consisting of: formyl, acetyl, benzoyl, phenoxyacetyl, and toluene sulfonyl, 2,4,6-trimethyl benzene sulfonyl. X can also be a phosphonium salt, such as tris(dimethylamino) phosphonium hexafluorophosphate or tetrafluoroborate, a uronium salt such as tetra-methyluronium hexafluorophosphate or tetrafluoroborate, and derivatives of these compounds. Additionally, X represents amino acids and amino-protected amino acid derivatives. However, $R_1$ cannot be methyl if $R_2$ and a, b, c, d and e are all represented by H, as the compound having this configuration, Mpp, has low activity, is generally formed in low yields and is not self-indicating.

Mpp is the methyl derivative, 1-phenyl-3-methyl-2-pyrazolin-5-one. Mpp and amino acid esters made therefrom were described by G. Losse et al. in *Peptidsyntheses mit Carboxylaktivierten Cbo-Aminosauren*, pp. 236-242 (1964), for preparing dipeptides by a solution synthesis method. Mpp esters are of low activity which do not possess self-indicating, colorimetric properties when used in SPPS.

The compounds described herein include enol and keto forms of the same materials. Enol forms are represented in the structural formulae, but names are given based on the keto form.

Preferred combinations of the present compounds include:

$c=NO_2$, $a=b=d=e=H$, $R_2=H$, and $R_1=$methyl or phenyl;

$c=$halogen, $a=b=d=e=H$, $R_2=H$ and $R_1=$methyl or phenyl;

$c=a=$halogen, $b=d=e=H$, $R_2=H$, and $R_1=$methyl or phenyl;

$c=a=NO_2$, $b=d=e=H$, $R_2=H$, and $R_1=$methyl or phenyl;

$a=b=c=d=e=H$, $R_2=H$, and $R_1=$phenyl or 4-nitrophenyl; and $a=b=d=e=H$, $c=$nitro, and $R_1$ and $R_2$ represent 4 methylene groups linking positions 3 and 4;

wherein X is any of the groups enumerated above.

These compounds include:

| Abbrev. | Name |
| --- | --- |
| Dpp | 1,3-diphenyl-2-pyrazolin-5-one |
| Ppn | 1-phenyl-3-(4'-nitrophenyl)-2-pyrazolin-5-one |
| Npp | 3-methyl-1-(4'-nitrophenyl)-2-pyrazolin-5-one |
| Pnp | 3-phenyl-1-(4'-nitrophenyl)-2-pyrazolin-5-one |
| Clmp | 3-methyl-1-(4'-chlorophenyl)-2-pyrazolin-5-one |
| PClp | 3-phenyl-1-(4'-chlorophenyl)-2-pyrazolin-5-one |
| DClmp | 3-methyl-1-(2',4'-dichlorophenyl)-2-pyrazolin-5-one |
| DClpp | 3-phenyl-1-(2',4'-dichlorophenyl)-2-pyrazolin-5-one |
| DNmp | 3-methyl-1-(2-',4'-dinitrophenyl)-2-pyrazolin-5-one |
| DNpp | 3-phenyl-1-(2',4'-dinitrophenyl)-2-pyrazolin-5-one |

The present 1-phenyl-pyrazolin-5-one derivatives are prepared by reaction of a phenyl hydrazine with an acylacetate ester. By this method modifications to the 1-phenyl ring and to $R_1$ are made. Substituents on the phenyl ring (a-e) can be, for example, H, nitro, halogens or $SO_3H$. To make Npp, for example, 4-nitrophenyl hydrazine is reacted with ethyl acetoacetate; to make PClp, 4-chlorophenyl hydrazine is reacted with ethyl-benzoylacetate. In this method, the phenyl hydrazine derivative is stirred in a suitable polar solvent (e.g. dimethyl formamide, dimethyl sulfoxide, methanol, ethanol or any simple alcohol, or glacial acetic acid, for example) optionally in the presence of acid (such as HCl) or base (such as pyridine or triethylamine). Warming is often necessary to effect complete solution, if so, the mixture is cooled to room temperature before the addition of 1 equivalent of an aryl or alkyl ester of an acylacetoacetate (e.g. ethyl acetoacetate, ethyl benzoylacetate). The nature of the acyl group dictates the substituent $R_1$; for example if Npp is required ethyl acetoacetate is used, if Pnp is required ethyl benzoyl acetate is used. The nature of the ester group does not influence the product prepared, it can be methyl, ethyl, any simple alkyl ester, phenyl, benzyl or an aryl containing group. The mixture is slowly heated to about 85°-90° C. Usually the reaction is left overnight in which case the temperature is reduced (to about 60° C.). The products crystallize from the reaction at the elevated temperature, and completely come out of solution when cooled to room temperature. The crystals of product are separated from the reaction mixture (e.g. by filtration), and the crystals are washed with solvent (e.g. alcohol. acetic acid or water) until the filtrate is colorless. The crystals are then dried.

Activated amino acid esters are prepared by esterification with the present 1-phenyl pyrazolin-5-one compounds through the carboxyl groups of the amino acid. The amino acids are generally amine-protected amino acids having the general formula:

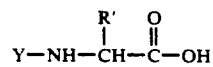

wherein R' represents the amino acid side chain and Y is a protective group. In a preferred embodiment of the present invention, Y is a protective group selected from the group consisting of: α-fluorenylmethyl-oxycarbonyl (Fmoc), t-butyloxycarbonyl (tBoc), 2-(4-biphenylyl)-2-propyloxycarbonyl (Bpoc) and nitropyridylsulfenyl (Npys). Activated amino acid esters are formed having the following general formula:

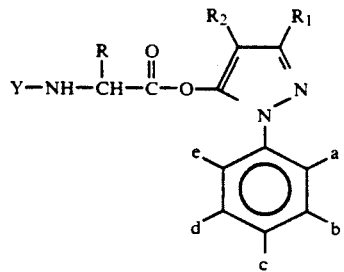

wherein $R_1$, $R_2$, a, b, c, d, e, R' and Y are groups as defined above. Activated esters having the above general formula can be made from any of the L- or D-known amino acids, or derivatives thereof. For example, amino acids having amide side chains (e.g., glutamine and asparagine) may have protective groups for the amide side chains in addition to protective groups for the α-amino group. Protective groups based on Taob (trialkoxy benzyl), as described in co-pending U.S. application Ser. No. 07/316,570 filed Feb. 27, 1989, are useful for this purpose in solid phase peptide synthesis. The present activated esters are particularly useful in Fmoc-solid phase peptide synthesis, where Fmoc is the α-amino protective group.

Activated amino acid esters are prepared by a variety of methods, for example, directly via the phenyl-pyrazolinone phosphonium salt or through intermediate unsymmetrical anhydrides, or with coupling reagents, such as diisopropylcarbodiimide (DIPCDI), DCCI or diphenylphosphoroazide. In the coupling reagent method, the 1-phenyl-pyrazolin-5-one derivative of choice (e.g., Npp or Pnp) is added to an organic solvent, such as dimethyl formamide (DMF), and warmed, if necessary, until the compound is completely dissolved.

The solution is cooled to room temperature and the protected amino acid of choice is added to the mixture, and stirred until dissolved. Generally, a slight excess of the 1-phenyl-pyrazoline-5-one compound is used. The mixture is then cooled to about −10° C. to about 20° C., and a coupling reagent, such as dicyclohexylcarbodiimide (DCCI), is added. The amount of coupling reagent added is equivalent to, or slightly in excess of, the amount of the amino acid. The reaction mixture is then agitated. Stirring is maintained until a precipitate is formed from the coupling agent and by-product of the esterification. For example if DCCI is used, the precipitate will be dicyclohexylurea. The precipitate is removed (e.g., by filtration) and the filtrate is evaporated. Upon evaporation the activated amino acid ester is crystallized from the residue. The crystals can then, optionally, be further purified, for example, by recrystallization from acetonitrile.

Twenty-seven different active esters of Fmoc-valine were prepared using a method similar to the above procedure. These active esters are listed in Table 1, along with their characteristics and relative activities. They are listed in order of their activity.

its suitability for the comparison of Fmoc-amino acid active esters. In this method, the test ester was mixed with an equimolar amount of Fmoc-Ile-OPFP ester, dissolved in DMF (dimethylformamide) or 3:1 DMF:trifluoroethanol, and added to a sample of swelled Gln(Tmob)-Ala-PAC-resin contained in a syringe column reactor system. After two hours the couplings were terminated, the terminal Fmoc groups removed, and the relative incorporation of Val and Ile determined by amino acid analysis after resin hydrolysis. The results, along with some physical characteristics of the active esters, are given in Table 1. Since Fmoc-Val-OPFP incorporated at 56.8%, then an active ester which incorporated more valine than this is more active than a PFP ester. This also applies to Dhobt (dihydrohydroxyoxobenzotriazine) and DNP (dinitrophenyl) esters. All other candidates shown in Table 1 including many regarded as highly efficient, are less active. Included in this lower division is the Mpp ester, which at 32.2% incorporation has slightly more than half the activity of PFP. The present chemical derivatives, however, have surprising and useful properties.

Table 2 lists the efficiency data of a variety of the

TABLE 1

Comparison of the Efficiency of Various Fmoc—VAL Active Esters

| | Ester Component | State | Solubility | m.p. | Val Inc. % |
|---|---|---|---|---|---|
| 1. | 2,4-Dinitrophenol | yellow crystals | *** | 112–113 | 95.0 |
| 2. | 3,4-dihydroxy-3-hydroxy-4-oxo-1,2,3-benzotriazine | off-white needles | *** | 106–109 | 82.3 |
| 3. | Pentafluorophenol | white crystals | ***** | 117–118 | 56.3 |
| 4. | 3-Methyl-1-phenyl-2-pyrazolin-5-one | white crystals | ***** | 148–149 | 32.3 |
| 5. | 2-Mercaptopyridine | pale yellow needles | ***** | 103–106 | 25.2 |
| 6. | 2,4-Dichloro-6-nitro phenol | orange crystals | *** | 112–114 | 24.4 |
| 7. | o-benzoic acid sulfimide (saccharine) | white crystals | ** | 186–188 | 22.4 |
| 8. | N-Hydroxy-phthalimide | white needles | ***** | 131–133 | 20.6 |
| 9. | 5,7-Dichloro-8-hydroxy quinoline | pale yellow foam | ***** | — | 15.1 |
| 10. | 2,6-Dichlor-4-nitro phenol | yellow crystals | *** | 155–157 | 13.1 |
| 11. | 2,4-Dinitro-o-cresol | yellow crystals | *** | 129–133 | 12.2 |
| 12. | 2,4,5-Trichlorophenol | white crystals | *** | 145–146 | 12.0 |
| 13a. | Pentachlorophenol | white crystals | * | 195–197 | 10.6 |
| 13b. | N-hydroxysuccinimide | white foam | ***** | — | 10.6 |
| 15. | N-Hydroxy-5-norbornene-2,3-dicarboxylic acid imide | white crystals | ***** | 155–157 | 10.3 |
| 16. | 2-Thiazoline-2-thiol | yellow foam | ***** | — | 9.0 |
| 17. | p-nitrophenol | pale yellow "sticky" crystals | ** | ? | 7.5 |
| 18. | 2-hydroxypyridine | white gum | *** | — | 5.3 |
| 19. | o-nitrophenol | yellow gum | ** | — | 5.2 |
| 20a. | 4-Hydroxyazobenzene | red-orange crystals | ** | 153–156 | <1.0 |
| 20b. | N-hydroxypiperidine | colorless oil | ***** | — | <1.0 |
| 20c. | 8-hydroxyquinoline | white gum | *** | — | <1.0 |
| 20d. | 5-Chloro-8-hydroxy quinoline | off-white crystals | *** | 111–112 | <1.0 |
| 20e. | Pyridine-4-carboxaldoxime | white crystals | ***** | 140–141 | <1.0 |
| 20f. | Pyridine-2-carboxaldoxime | white foam | *** | — | <1.0 |
| 20g. | Thiophenol | white needles | ***** | 133–134 | <1.0 |

*incompletely soluble in DMF at 0.1M
**soluble 0.2M in DMF r. temp. with 5 minutes sonication
***soluble 0.2M in DMF r. temp. with 2 minute sonication
****soluble 0.2M in DMF r. temp. without sonication
*****Highly soluble in DMF The method used to compare activities follows essentially the method described by D. Hudson in *Journal of Organic Chemistry*, 53:617 (1988) for the comparison of the efficiencies of different coupling reagents. Several modifications were made to this procedure to improve present modified 1-phenyl-pyrazolin-5-one enol esters. Previously tested esters were included as controls, and close correspondance between the values in the separate experiments was obtained.

TABLE 2

The Relative Efficiency of Several Phenyl-Pyrazolinone Esters Compared to Other Selected Active Esters

| Ester | R1 | R2 | (a-e) | m.p. | solubility | % Val (in DMF) | % Val (DMF:TFE 3:1) |
|---|---|---|---|---|---|---|---|
| Pnp | Ph | H | c = NO2 | 168-169 | *** | 95* | 95* |
| DnP | — | — | — | 112-113 | *** | 95 | 95 |
| Npp | Me | H | c = NO2 | 195-197 | ** | 92 | 86 |
| Dhbt | — | — | — | 106-109 | *** | 82 | n.d. |
| PClp | Ph | H | c = Cl | 112-113 | *** | 77 | 82 |
| Dpp | Ph | H | all H | 147-149 | *** | 59 | 68 |
| PFP | — | — | — | 117-118 | *** | 56 | 56 |
| DClpp | Ph | H | a = c = Cl | 146-149 | *** | 50 | 62 |
| Mpp | Me | H | all H | 148-149 | *** | 32 | 40 |
| Npc | (CH$_2$)$_4$ | | c = NO$_2$ | 183-185 | ** | 7.4 | 9.8 |

*Identical values have been obtained when tBoc—Val—OPnp (m.p. 120-122) was used in place of Fmoc—Val—Opnp.
****soluble 0.2M in DMF r. temp. without sonication
***soluble 0.2M in DMF r. temp. with 2 minute sonication
**soluble 0.2M in DMF r. temp. with 5 minutes sonication.

As shown in Table 2, all but one variant are of higher activity than PFP. In the Npc derivative, formed by reaction of 2-carbethoxycyclohexanone with 4-nitrophenylhydrazine, the distortion of the pyrazol ring caused by bridging R1 and R2 with 4-methylene groups diminishes the aromaticity of the system, and dramatically reduced its activity. Correspondingly, a minor change, replacement of methyl with phenyl, gives extended conjugation, and a marked increase in activity, with retention of good solubility and high crystallinity. In the chlorinated series, comparing DClpp with PClp, the 4-monochloro derivative is far more active than the 2,4-dichloro derivative. This is presumably because the bulk and electron-rich nature of the 2-Cl group inhibits the hydrogen bonding of the incoming amino group with the nitrogens of the pyrazol ring. Npp and Pnp are both very highly active derivatives indeed, comparable to the super-active but relatively unstable Dnp derivative. Pnp is slightly more active, and of higher solubility than Npp. Also the tBoc-Val-OPnp ester shows good crystallinity, and identical activity.

The present esters are between 10 and 20 times more active that PFP esters, are highly crystalline, stable on storage, relatively inert to hydroxyl groups, and possess self-indicating properties. The Npp anion in DMF solution, has an extinction co-efficient of $5.3 \times 10^3$ at 488 nm, which accounts for the blood-red color observed in incomplete couplings, a wavelength which is well removed from any possible source of interference (e.g. by unreacted ester).

Table 2 also introduces a modification in the competition method: in the usual procedure (% Val incorporated, penultimate column) the competition experiment is performed in DMF following complete dissolution of the mixed components. In the modified method (last column), dissolution was effected in 3:1 mixture of DMF/trifluoroethanol (TFE), and the competition performed after 2 minutes. The relative incorporation in the PFP control was unaffected, and couplings still go to completion. However the relative incorporation of the 1-phenyl-pyrazolin-5-one derivatives increases, except with Pnp and Npp. The increase can be attributed to the partial decomposition of the PFP esters in this mixture, whereas the 1-phenyl-pyrazolin-5-one derivatives are more stable. The use of this solvent combination, which breaks down hydrogen bonded secondary structures of the resin-bound peptides, ensures that most couplings go at a more uniform rate, and, when combined with an active derivative, this rate will be very high.

The present 1-phenyl-pyrazolin-5-one derivatives can be used as additives to known coupling reagents, can constitute new coupling reagents or be used as active esters of amino acids. As new coupling reagents, in solid phase peptide synthesis for example, where X is a phosphonium salt such as tris(dimethylamino)phosphonium hexafluorophosphate, the composition is added, along with one equivalent of a tertiary base to non-preactivated, α-amino-protected amino acid derivatives (also called "free" protected amino acids) to the SPPS system. The resultant activated species is then added to the support-bound peptide to effect coupling and chain elongation, and simultaneously liberating the 1-phenyl-pyrazolin-5-one moiety, which acts as the colormetric indicator. Phosphonium derivatives of the present 1-phenyl-pyrozolin-5-one compounds can also be used as an alternative method to the DCCI procedure described herein for their preparation.

Activated amino acids prepared by the above-described process are used in solid-phase peptide synthesis. In this method, a first amino acid (generally an α-amine-protected amino acid) is covalently attached through its carboxyl group to a synthesis resin or bead. Examples of synthesis resins include the Fmoc-compatible polystyrene PAC and PAL resins (Milligen/Biosearch Novato, Calif.), tBoc-compatible polystyrene resins, MBHA and PAM resins, as well as polydimethyl acrylamine in encapsulated (Pepsynk) or free forms, functionalized ceramic particles, HPCC and other silicas, controlled pore glass and polyethyleneglycol-polystyrene copolymers. The general synthesis cycle then consists of deprotection of the α-amine group of the amino acid, washing, and, if appropriate, neutralization, followed by reaction with the next carboxyl-activated amino acid to be added. Each successive amino acid is attached to the terminal nitrogen of the resin-bound amino acid or peptide chain through the carbonyl carbon of its carboxylic acid group. The activating group is liberated during the coupling reaction and is released into the reaction medium, where it acts as an indicator to monitor the completeness of the reaction, because it is ionized by unreacted amino groups present in the system. For example, if Npp-protected amino acids are used, Npp liberated during the coupling reaction is ionized by unreacted amino groups, and in the ionized state is an intense red color. Upon completion of the reaction as all of the free amino groups are consumed, Npp becomes non-ionized and fades to a gold color. Thus, the reaction is self-indicating, eliminating the need to stop the reaction to test for free amino groups.

In another embodiment of the above method, a 1-phenyl-pyrazolin-5-one compound in the enol form (that is, where X=H) is not used as an amino acid activating group, but is added separately to an SPPS system as a colormetric indicator to monitor the reaction for completeness.

In another embodiment of the SPPS method, 1-phenyl-pyrazolin-5-one compounds are prepared as coupling reagents, in which X is a positively charged species. Useful reagents include phosphonium and uronium salts, such as tris(dialkyl amino) phosphonium salts and tetralkyluronium salts compounded with tetrafluoroborate or hexafluorophosphate counterions. The alkyl groups are generally methyl or ethyl groups, but can also be constituted of small ring systems such as pyrrolidine and piperidine. An adduct is formed by reacting the 1-phenyl-pyrazolin-5-one anion with an activated derivative (e.g., hexamethylphosphonium chloride or tetramethyluronium chloride) to give the desired coupling reagent. This hybrid is then added to the free amino acid activating it for coupling and liberating the 1-phenyl-pyrazolin-5-one component which then provides colorimetric monitoring of the extent of the reaction with the amino group of the resin-bound peptide. When coupling is complete, the red color of the anion fades to a gold color. These hybrid coupling reagents are efficient and self-indicating coupling reagents in SPPS, and provide an excellent method for the direct synthesis of the actual active esters themselves. The above-described DCCI method is relatively difficult to perform and to scale-up. Utilizing the hybrid reagents, then activating the amino acid derivatives in the absence of amino groups, gives the active esters, which are then isolated by precipitation from water, and filtration.

In another embodiment of the present method, the extent of coupling in either solution phase or solid phase synthesis can be monitored and, following indication of completeness subsequent steps in the assembly process of the peptide initiated. This results in the synthesis of high quality peptides in the minimum time required. The high wavelength at which the enol anions absorb, e.g., 488 nm with Npp, means that other absorbing species will not interfere with measurement. As an example, on a 0.1 mmol scale, when coupling is 99% complete, the absorption at 488 nm should be 2 O.D. units. Consequently, monitoring to this degree of completion, or to even higher levels of completion, is accessible. This can be achieved by several methods. For example, a light source, filter and photoelectric cell can be arranged in a linear manner with the reaction chamber placed in the direct path. Alternatively, the change in absorption of light reflected from the glass surface of the reactor can be used, or, most sensitively, the light source can be embedded within a transparent reactor and the detector configured as a cylinder around the reactor.

Some of the applications of the present 1-phenyl-pyrazolin-5-one derivatives include: as active esters of all N-protected amino-acids in both solution and solid-phase synthesis; as additives to carbodiimide, (benzotriazolyloxy)tris(dimethylamino)phosphonium hexafluorophosphate (BOP) and active ester couplings; as components of hybrid reagents; and as coupling completion indicators for any type of peptide coupling. Acyl derivatives of the present compounds can also be used as chain terminating and capping reagents in both peptide and DNA synthesis. Such derivatives may, additionally, be important in directly preparing nucleoside monomers. Derivatives with alkyl substituted phosphoramides and ureas yield analogues of BOP and HBTU (2-(1H-benzotriazol-1-yl)-1,1,3,3-tetramethyluronium hexafluoro-phosphate) coupling agents which are self-indicating, having improved reactivity and stability. For example, sulfonyl derivatives of the present 1-phenyl-pyrazolin-5-ones are good coupling agents in phosphate-triester-mediated DNA synthesis. Use of mesitylene sulfonyl 3-methyl-1-(4'-nitrophenyl)-2-pyrazolin-5-one (MS-Npp), for example, yields superior results. Those derivatives having a suitable pK, such as Npp, can serve as useful amidite activators.

The invention is further illustrated by the following Examples.

EXAMPLE 1

Preparation of 1-phenyl-pyrazolin-5-ones

A substituted phenyl hydrazine is condensed, by heating, with an acylacetoacetate aryl or alkyl ester to give the desired derivative. This is illustrated by the preparation of Npp given below.

4-Nitrophenyl hydrazine (containing 10% water, 1.7 grams, 10 mmol) was stirred in glacial acetic acid (20 mL) and warmed to 35° C. until complete solution resulted. The stirred mixture was cooled to room temperature and ethyl acetoacetate (1.30 g, 1.27 mL, 10 mmol) was added rapidly. After 10 minutes at room temperature the flask was placed in an oil bath and heating commenced to 85° C. over 30 minutes. After an additional 30 minutes at this temperature a dense yellow precipitate formed. The reaction was left at 80° C. for 2 hours, then stirred overnight at 60° C., and cooled to room temperature. The crystals were collected by filtration, washed with several small portions of acetic acid until the filtrate was colorless, then washed with ether and air dried to give 2.00 grams Npp, 91% yield, m.p. 219°-220° C.

EXAMPLE 2

Preparation of Phenyl Pyrazolinone Amino Acid Esters

This method is applicable to any N- and side-chain protected amino acid and to all ester components. The method uses dicyclohexylcarbodi-imide and the 2 components in dimethylformamide solvent. In the following example Fmoc-L-Val-ONpp is prepared as follows:

3-methyl-1-(4'-nitrophenyl)-2-pyrazolin-5-one (1.12 grams, 5.1 mmol) was dissolved in DMF (25 mL) by warming to about 45° C. The clear dark orange solution which formed was stirred, cooled to room temperature and Fmoc-L-valine (1.7 grams, 5 mmol) was added. When this had all dissolved, the mixture was placed in a bath at 15° C., and dicyclohexyl-carbodiimide (1.07 grams 5.05 mmol) was added to the vigorously mixed reaction. Stirring was continued for 2 days at 15° C. The precipitated dicyclohexylurea was removed by filtration and the filtrate evaporated. The Npp ester crystallised immediately. It was dried briefly in high vacuum, then recrystallised from 100 mL of hot acetonitrile, giving 2.2 grams of Fmoc-Val ONpp, 80% yield, m.p. 195°-197° C.

The following Table 3 shows some additional Fmoc-amino acid Npp esters (designated as —ONpp) prepared by the above method:

TABLE 3

ACTIVATED FMOC-AMINO ACID NPP ESTERS

| Amino Acid | MOL. WT. | YIELD | M.P. (°C.) |
|---|---|---|---|
| Fmoc—Gly—ONpp | 498 | 86% | 164–167 |
| Fmoc—L-Ala—ONpp | 512 | 78% | 185–187 |
| Fmoc—L-Ile—ONpp | 554 | 83% | 172–173 |
| Fmoc—L-Asp(OBut)—ONpp | 612 | 53% | 132–133 |
| Fmoc—L-Tyr(But)—ONpp | 660 | 73% | 139–141 |
| Fmoc—L-Gln(Tmob)—ONpp | 750 | 75% | 166–167 |
| Fmoc—L-Val—ONpp | 540 | 80% | 195–197 |

EXAMPLE 3

Use of ONpp Esters in Automated Solid-Phase Peptide Synthesis: Synthesis of the Peptide H-Val-Ala-Ile-Asp-Tyr-Ile-Gly-NH₂

The synthesis was performed on an Excell peptide synthesizer with standard reagents and operating protocols except where noted. All N-methylmorpholine and HOBt solutions (activator and prewash) were replaced with HPLC grade DMF. No activation or prewash is required with this method. Each cartridge was packed with 0.5 mmol of the Npp ester alone (no BOP or HOBt required).

Visual inspection during coupling showed coupling completeness within 5 minutes. The gold-colored active ester solution, upon entering the reaction column caused the resin to turn an intense red color, which faded to a gold color as coupling proceeded. After the synthesis was completed, as indicated by the presence of the gold color, the resin was cleaved with Reagent A (TFA/DMS/DCM, 14:1:5) for two hours. The resin was filtered, the filtrate was evaporated, and the product peptide lyophilized from glacial acetic acid. This gave 120 mg (100%) of peptide with HPLC and AAA behavior consistent with high purity.

EXAMPLE 4

Use of Npp As An Indicator In Solid-Phase Peptide Synthesis

The method described Example 3 was modified to provide a prewash with a solution of 1 gram of Npp in 200 ml of DMF. The cartridges were packed with 0.25 mmol of the Npp esters alone (a 2.5-fold excess). Couplings were performed for 30 minutes. The column became intensely red during the prewash, and faded to the gold color during coupling. This is an example of use of Npp as an indicator; although this specific example used Npp esters for coupling, all other methods using Npp would have shown the same change. Couplings were complete within 5–10 minutes. Cleavage and analysis gave comparable yield and analytical data to those obtained in Example 3.

EXAMPLE 5

Phenoxyacetic Acid Npp Ester (PAC-ONpp)

Following closely the method of Example 2, Npp (1.12 grams, 5.05 mmol) was dissolved in DMF (25 mL) and phenoxyacetic acid (0.76 gram, 5 mmol) added to the stirred solution which was placed at 15° C. DCCI (1.07 grams) was added and the mixture stirred overnight. The suspension was left at 4° C. for 2 hours then filtered, and the filtrate evaporated. The residue was dissolved in 20 mL of anhydrous ether and left at 4° C. overnight. Needlelike crystals of PAC-ONpp (m.p. 94–96) were deposited and were isolated in high yield and purity.

When this procedure was applied to Mpp no product was obtained.

EQUIVALENTS

Those skilled in the art will recognize, or be able to ascertain using no more than routine experimentation, many equivalents of the invention described herein. Such equivalents are intended to be encompassed within the scope of this invention.

I claim:

1. A pryazolinone derivative having self-indicating chromogenic properties having the general formula:

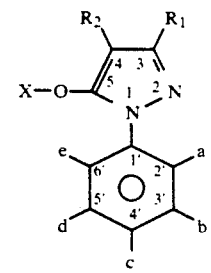

wherein:
i. $R_1$ is selected from the group consisting of: H, methyl, ethyl, isopropyl, phenyl, nitrophenyl, chlorophenyl and benzyl;
ii. $R_2$ is selected from the group consisting of: H, methyl, ethyl, isopropyl, phenyl, nitrophenyl, chlorophenyl, benzyl, halogens and $NO_2$;
iii. a, b, c, d and e are independently selected from the group consisting of H, $NO_2$ halogens and $SO_3H$; and
iv. X is tris(dimethylamino) phosphonium hexafluorophosphate, tris(dimethylamino) phosphonium tetrafluoroborate, tetramethyluronium hexafluorophosphate or tetramethyluronium tetrafluoroborate;

wherein $R_1$ is not methyl if $R_2$, a, b, c, d and e are all H.

2. A compound of claim 1, wherein a, b, d and e are H, c is $NO_2$, $R_2$ is H and $R_1$ is $CH_3$ or phenyl.

3. A compound of claim 1, wherein a, b, d and e are H, c is Cl, $R_2$ is H and $R_1$ is $CH_3$ or phenyl.

4. A compound of claim 1, wherein a and c are both Cl, b, d and e are H, $R_2$ is H and $R_1$ is $CH_3$ or phenyl.

5. A compound of claim 1, wherein a and c are both $NO_2$, b, d and e are H, $R_2$ is H and $R_1$ is $CH_3$ or phenyl.

6. A compound of claim 1, wherein a, b, c, d and e are H, $R_2$ is H and $R_1$ is phenyl or 4-nitrophenyl.

7. A compound of claim 1, wherein a, b, d and e are H, c is $NO_2$, and $R_1$ and $R_2$ represent 4 methylene groups linking ring positions 3 and 4.

* * * * *